United States Patent
Bush et al.

(10) Patent No.: US 10,723,624 B2
(45) Date of Patent: Jul. 28, 2020

(54) PROCESS FOR PREPARATION OF NITROGEN OXIDES AND NITRIC ACID FROM NITROUS OXIDE

(71) Applicant: Ascend Performance Materials Operations LLC, Houston, TX (US)

(72) Inventors: Gregory E. Bush, Pensacola, FL (US); Darrick K. Elmore, Pensacola, FL (US); Mikhail I. Khramov, Pensacola, FL (US)

(73) Assignee: Ascend Performance Materials Operations LLC, Houston, TX (US)

(*) Notice: Subject to any disclaimer, the term of this patent is extended or adjusted under 35 U.S.C. 154(b) by 0 days.

(21) Appl. No.: 16/208,926

(22) Filed: Dec. 4, 2018

(65) Prior Publication Data

US 2019/0169029 A1    Jun. 6, 2019

Related U.S. Application Data

(60) Provisional application No. 62/594,743, filed on Dec. 5, 2017.

(51) Int. Cl.

| | | |
|---|---|---|
| *C01B 21/38* | (2006.01) | |
| *C01B 21/24* | (2006.01) | |
| *C07C 51/31* | (2006.01) | |
| *B01J 12/00* | (2006.01) | |
| *B01J 19/00* | (2006.01) | |
| *C01B 21/36* | (2006.01) | |

(52) U.S. Cl.
CPC ............ *C01B 21/38* (2013.01); *B01J 12/005* (2013.01); *B01J 19/0013* (2013.01); *C01B 21/24* (2013.01); *C01B 21/36* (2013.01); *C07C 51/316* (2013.01)

(58) Field of Classification Search
CPC ...... C07C 51/316; C07C 55/14; B01J 12/005; B01J 19/0013; C01B 21/24; C01B 21/36; C01B 21/38
See application file for complete search history.

(56) References Cited

U.S. PATENT DOCUMENTS

| | | | |
|---|---|---|---|
| 4,139,595 A | 2/1979 | Vaseen | |
| 5,429,811 A | 7/1995 | Alarcon et al. | |
| 5,472,680 A * | 12/1995 | Reimer .................. | C01B 21/24 423/235 |
| 5,711,859 A | 1/1998 | Caramel et al. | |
| 6,328,941 B1 | 12/2001 | Watzenberger et al. | |
| 6,500,398 B1 | 12/2002 | Tagawa et al. | |
| 6,534,029 B1 | 3/2003 | Klein et al. | |
| 2013/0011299 A1 | 1/2013 | Hsu et al. | |
| 2013/0171272 A1 | 7/2013 | Koerber et al. | |

FOREIGN PATENT DOCUMENTS

| | | |
|---|---|---|
| CA | 2553812 A1 | 12/2007 |
| CN | 105126608 A | 12/2015 |
| JP | 1986 257940 | * 11/1986 |
| JP | S61-257940 A | 11/1986 |
| JP | 2012-197205 A | 10/2012 |
| WO | 95/20541 A1 | 8/1995 |
| WO | 2011/056548 A2 | 5/2011 |
| WO | 2011/056576 A2 | 5/2011 |
| WO | 2013/028668 A2 | 2/2013 |

OTHER PUBLICATIONS

JP1986 257940 translated (Year: 1986).*
Shimizu et al., "Abatement technologies for N2O emissions in the adipic acid industry," Chemosphere—Global Change Science 2, 425-434 (2000).
International Search Report issued in corresponding International Patent Application No. PCT/US2018/063732 dated Feb. 14, 2019.
Written Opinion issued in corresponding International Patent Application No. PCT/US2018/063732 dated Feb. 14, 2019.
Mainhardt, "N2O Emissions from Adipic Acid and Nitric Acid Production," Good Practice Guidance and Uncertainty Management in National Greenhouse Gas Inventories, 183-195 (1996).

* cited by examiner

*Primary Examiner* — Jafar F Parsa
*Assistant Examiner* — Blaine G Doletski
(74) *Attorney, Agent, or Firm* — Kilpatrick Townsend & Stockton LLP

(57) ABSTRACT

Described herein is an improved conversion of nitrous oxide ($N_2O$) present as a by-product in a chemical process to $NO_x$ which can be further converted to a useful compound or material, such as nitric acid.

15 Claims, No Drawings

PROCESS FOR PREPARATION OF NITROGEN OXIDES AND NITRIC ACID FROM NITROUS OXIDE

BACKGROUND OF THE INVENTION

Nitrous oxide ($N_2O$) is a naturally occurring greenhouse gas with a warming potential per molecule of approximately 290 times that of a carbon dioxide molecule. Pure $N_2O$ is known to be explosive. Several industrial processes generate $N_2O$ as a by-product such as the preparation of adipic acid from cyclohexanone/cyclohexanol and nitric acid ($HNO_3$). Adipic acid is a starting material in the manufacture of nylon 66, which has widespread use throughout the world as a component in, for example, home furnishings (carpets, upholstery, bedspreads and the like), apparel, tire cord, conveyor belts, seat belts, air bags, parachutes, ropes and nets, sleeping bags, tarpaulins, tents and auto parts. The adipic acid is typically prepared in a two-stage process, where the first stage involves the oxidation of cyclohexane to a cyclohexanone/cyclohexanol mixture, and the second stage involves oxidation of this mixture with nitric acid to produce adipic acid. Nitrous oxide, nitrogen oxides ($NO_x$, collectively nitrogen monoxide (NO) and dioxide ($NO_2$)) and water ($H_2O$) are the chief by-products generated during this oxidation reaction. Notably, $NO_x$ is also a pollutant and its emission is subject to strict regulations.

Current methodologies practiced by large scale generators of $N_2O$ for conversion of the $N_2O$ to a more environmentally friendly form include (i) catalytically decomposing the $N_2O$ to nitrogen gas ($N_2$) and oxygen gas ($O_2$) which are released into the atmosphere; or (ii) treating a $N_2O$-containing offgas with natural gas in a thermal reduction unit to form nitrogen gas, carbon dioxide and water ($4\ N_2O+CH_4 \rightarrow 4\ N_2+CO_2+2\ H_2O$), which is then released into the atmosphere.

Both of these protocols have the drawback of converting the $N_2O$ to a non-useful form (nitrogen gas) which is discarded. There is, however, an ongoing need to recover and, if possible, to recycle or use in an economically effective manner the $N_2O$ and $NO_x$ components contained in an industrial waste gas or an offgas. U.S. Pat. No. 5,429,811 and Japanese Published Patent Application No. S61-257940 represent examples of conventional technologies for the thermal decomposition of $N_2O$ to $NO_x$.

The present invention provides a significant improvement over conventional techniques for the preparation of nitric acid from $N_2O$ (via a $NO_x$ intermediate) and is especially effective when conducted on an industrial-scale. In the particular application of the present invention where the source of the initial $N_2O$-containing reactant composition is the offgas from the production of adipic acid, the conversion of the $N_2O$ in the offgas to $NO_x$ and ultimately to nitric acid represents an efficient and safe recycling of the nitric acid starting material used in the production of adipic acid. This process is more cost effective than existing processes where the $N_2O$ by-product is destroyed by conversion to either unusable $N_2$ gas or to nitric acid under reaction conditions not readily amenable to industrial level scale-up.

SUMMARY OF THE INVENTION

An aspect of the present invention is a process for preparing adipic acid, comprising:
reacting at least one of cyclohexanone and cyclohexanol with nitric acid to produce adipic acid and an offgas comprising at least 10 mol % nitrous oxide ($N_2O$);
converting the $N_2O$ present in the offgas to a nitrogen oxide ($NO_x$) (x=1 or 2) in a yield of greater than 15% by passing the offgas through a reactor operating at a temperature of 2200° F. or greater;
converting the $NO_x$ to nitric acid; and
optionally recycling the nitric acid to produce additional adipic acid.

Another aspect of the present invention is a process for preparing adipic acid, comprising:
reacting cyclohexanone, cyclohexanol or a mixture thereof with nitric acid to produce adipic acid and an offgas comprising 20 to 80 mol % nitrous oxide ($N_2O$);
converting the $N_2O$ present in the offgas to a nitrogen oxide ($NO_x$) (x=1 or 2) in a yield of greater than 15% by passing the offgas through a reactor operating at a temperature of 2200° F. or greater;
converting the $NO_x$ to nitric acid; and
recycling the nitric acid for production of additional adipic acid, wherein the process results in a greater than 10% reduction in $N_2O$ emission.

In an exemplary embodiment, the reactor operates at an internal temperature range of 2000 to 3500° F., such as 2200 to 3500° F., such as 2500 to 3500° F., such as 2300 to 3300° F., such as 2400 to 3300° F., such as 2500 to 3300° F., such as 2600 to 3300° F., such as 2500 to 3200° F., such as 2500 to 3000° F., such as 2600 to 3200° F., such as 2600 to 3000° F., such as 2400 to 3000° F., such as 2400 to 2800° F.

In an exemplary embodiment, the offgas prior to passing through the reactor comprises 10 to 99 mol % $N_2O$, such as 15 to 90 mol %, such as 20 to 90 mol %, 30 to 80 mol %, such as 30 to 70 mol %, such as 30 to 50%, such as 40 to 95 mol %, such as 40 to 85 mol %, such as 40 to 80 mol %, such as 40 to 75 mol %, such as 40 to 70 mol %, such as 40 to 60%, such as 35 to 70 mol %, such as 40 to 70 mol %, such as 40 to 80 mol %, such as 50 to 80 mol %, such as 60 to 80 mol %.

In an exemplary embodiment, the yield of $NO_x$ from $N_2O$ is greater than 15%, such as greater than 17%, such as greater than 18%, such as greater than 19%, such as greater than 20%, such as greater than 21%, such as greater than 22%, such as greater than 23%, such as greater than 24%, such as greater than 25%, such as greater than 27%, such as greater than 30%, such as greater than 35%. In an exemplary embodiment, the yield of $NO_x$ from $N_2O$ is in a range of 20 to 35%, such as 20 to 30%, such as 20 to 25%.

In an exemplary embodiment, the offgas prior to passing through the reactor further comprises less than 2 mol % water, such as less than 1 mol %, such as less than 0.5 mol %, such as less than 0.2 mol %. In an exemplary embodiment, the offgas comprises between 0 and 2 mol % water, such as 0.1 to less than 2 mol %, such as between 0 and 1 mol %, such as between 0 and 0.5 mol %.

In an exemplary embodiment, the offgas has a residence time in the reactor of less than 150 seconds, such as less than 120 seconds, such as less than 100 seconds, such as less than 80 seconds, such as less than 60 seconds, such as less than 30 seconds, such as less than 15 seconds, such as less than 10 seconds, such as less than 5 seconds, such as less than 2 seconds, such as less than 1 second, such as less than 0.5 seconds, such as less than 0.1 seconds, such as less than 0.05 seconds. In an exemplary embodiment, the offgas has a residence time in the reactor of between 0.01 to less than 60 seconds, such as between 0.05 to less than 60 seconds, such as between 0.5 to less than 30 seconds, such as between 0.5 to less than 15 seconds, such as between 1 to less than 10 seconds, such as between 1 to less than 5 seconds.

In an exemplary embodiment, the reactor has a length to diameter (L/D) ratio of greater than 2, such as greater than 4, such as greater than 8, such as greater than 10, such as greater than 12, such as greater than 14, such as greater than 18, such as greater than 20, such as greater than 25, such as greater than 30, such as greater than 40, such as greater than 50. In an exemplary embodiment, the L/D ratio is in a range of 3 to 40, such as 3 to 30, such as 3 to 25, such as 6 to 25, such as 6 to 20, such as 6 to 15, such as 8 to 15, such as 10 to 15.

In an exemplary embodiment, the reactor operates under adiabatic or substantially adiabatic conditions.

In an exemplary embodiment, the outside surface temperature of the reactor is greater than 100° F., such as greater than 150° F., such as greater than 200° F., such as greater than 250° F. In an exemplary embodiment, the surface temperature of the reactor is in a range of 150 to 350° F., such as 150 to 300° F., such as 200 to 250° F.

In an exemplary embodiment, the reactor operates at a pressure of less than 15 psig, such as less than 10 psig, such as less than 5 psig. In an exemplary embodiment, the reactor operates at a pressure of between 0.5 to 10 psig, such as between 1 to 5 psig.

In an exemplary embodiment, the reactor is a plug flow reactor. In another exemplary embodiment, the reactor is substantially plug flow but is configured to induce backflow in at least a portion of the gas stream passing through the reactor.

In an exemplary embodiment, the offgas passes through the reactor at a rate of greater than 500 pounds per hour (pph), such as greater than 1000 pph, such as greater than 1500 pph, such as greater than 2000 pph, such as greater than 2500 pph, such as greater than 3000 pph, such as greater than 5000 pph, such as greater than 10,000 pph, such as greater than 20,000 pph, such as greater than 30,000 pph, such as greater than 40,000 pph, such as greater than 50,000 pph, such as greater than 60,000 pph, such as greater than 70,000 pph, such as greater than 80,000 pph, such as greater than 90,000 pph. In another exemplary embodiment, the offgas passes through the reactor at a rate of 3000 to 100,000 pph, such as 3000 to 80,000 pph, such as 3000 to 50,000 pph, such as 3000 to 30,000 pph, such as 3000 to 20,000 pph.

In an exemplary embodiment, the offgas prior to passing through the reactor further comprises less than 5 mol % $NO_x$, such as less than 2 mol %, such as less than 1 mol % $NO_x$, such as less than 0.5 mol % $NO_x$, such as less than 0.1 mol % $NO_x$. In an exemplary embodiment, the offgas prior to passing through the reactor further comprises between 0 to 2 mol % $NO_x$, such as between 0.1 to 1 mol % $NO_x$.

In an exemplary embodiment, the offgas prior to passing through the reactor is preheated to greater than 500° F., such as greater than 700° F., such as greater than 900° F., such as greater than 1000° F. In an exemplary embodiment, the offgas prior to passing through the reactor is preheated to less than 1500° F. In an exemplary embodiment, the offgas prior to passing through the reactor is preheated to greater than 700° F. but less than 1500° F., such as greater than 900° F. but less than 1500° F., such as greater than 900° F. but less than 1200° F.

In an exemplary embodiment, the offgas is pressurized prior to passage through the reactor. In another exemplary embodiment, the offgas is not pressurized prior to passage through the reactor.

In an exemplary embodiment, heat generated in the reactor during conversion of $N_2O$ to $NO_x$ provides at least a substantial portion of the heat used to preheat the offgas prior to entry of the offgas into the reactor. In an exemplary embodiment, heat generated in the reactor during conversion of the $N_2O$ to $NO_x$ provides substantially all of the heat used to preheat the offgas prior to entry of the offgas into the reactor.

In an exemplary embodiment, an interior surface of the reactor comprises a ceramic material.

In an exemplary embodiment, the offgas prior to passing through the reactor is treated to reduce the amount of at least one of the water and $NO_x$ components present in the offgas.

In an exemplary embodiment, the offgas prior to passing through the reactor is diluted with air.

Another aspect of the present invention is a process for preparing an intermediate nitric acid stream from nitrous oxide ($N_2O$), comprising:
preheating a feedgas comprising at least 10 mol % $N_2O$ and less than 1.0 mol % water to a temperature of greater than 900° F., followed by
passing the feedgas through a reactor operating at a temperature range sufficient to convert the $N_2O$ to nitrogen oxide ($NO_x$) (x=1 or 2) in a yield of greater than 15%; and
converting the $NO_x$ present in the resulting product gas stream to nitric acid.

Another aspect of the present invention is a process for preparing nitric acid from nitrous oxide ($N_2O$), comprising:
concentrating $N_2O$ present in a feedgas to at least 10 mol % $N_2O$;
passing the feedgas through a reactor operating at a temperature of 2200° F. or greater to provide nitrogen oxide ($NO_x$) (x=1 or 2) in a yield of greater than 15%; and
converting the $NO_x$ to nitric acid.

In an exemplary embodiment, the process further comprises cooling the temperature of the product gas stream exiting the reactor to a temperature of less than 250° F., such as less than 200° F., such as less than 150° F., such as less than 100° F.

In an exemplary embodiment, the cooled product gas stream is also compressed.

In an exemplary embodiment, the feedgas comprises at least 30 mol % $N_2O$, such as at least 40 mol %, such as at least 50 mol %, such as at least 60 mol %, such as at least 70 mol %, such as at least 80 mol %, such as at least 90 mol %.

Another aspect of the present invention is a process for preparing a nitrogen oxide ($NO_x$) (x=1 or 2) from nitrous oxide ($N_2O$), comprising:
preheating a feedgas comprising greater than 40 mol % $N_2O$ in a preheater to a temperature of at least 900° F.;
generating a reaction product stream by passing the feedgas at a rate greater than 1000 pph through a reactor operating at a temperature sufficient to convert the $N_2O$ to $NO_x$ in a yield of greater than 15%;
passing the reaction product stream through a first quench unit, where the reaction product stream is cooled to a temperature sufficient to heat the feedgas in the preheater to a temperature of at least 900° F., followed by passing the cooled reaction product stream through the preheater to heat the feedgas to a temperature of at least 900° F.; and
quenching the cooled reaction product stream to a temperature of less than 300° F. in a second quench unit.

In an exemplary embodiment, the preheater is situated downstream (i.e., at the exit end) of the reactor between the first and second quench units and the configuration of the system is such that the feedgas enters through the preheater, (optionally after passing through a scrubbing unit) prior to entry into the reactor. In an exemplary embodiment, a burner is situated upstream (i.e., at the entrance end) of the reactor for providing a hot air and gas (e.g., methane) mixture into the reactor via a separate line from the feedgas. In an exemplary embodiment, the means for converting the $NO_x$ present in the product composition into nitric acid is situated downstream of the second quench unit.

In an exemplary embodiment, the feedgas has a $N_2O$ concentration of greater than 60 mol %, such as greater than 80 mol %. In an exemplary embodiment, the feedgas has a $N_2O$ concentration of less than 90 mol %, such as less than 85 mol %.

In an exemplary embodiment, the feedgas passes through the reactor at a rate of greater than 1500 pph, such as greater than 2000 pph, such as greater than 2500 pph, such as greater than 3000 pph, such as greater than 5000 pph, such as greater than 10,000 pph, such as greater than 20,000 pph, such as greater than 30,000 pph, such as greater than 40,000 pph, such as greater than 50,000 pph, such as greater than 60,000 pph, such as greater than 70,000 pph, such as greater than 80,000 pph, such as greater than 90,000 pph. In another exemplary embodiment, the feedgas passes through the reactor at a rate of 3000 to 100,000 pph, such as 3000 to 80,000 pph, such as 3000 to 50,000 pph, such as 3000 to 30,000 pph, such as 3000 to 20,000 pph.

In an exemplary embodiment, the $N_2O$ is converted to $NO_x$ in a yield of greater than 15%, such as greater than 20%, such as greater than 25%, such as greater than 30%, such as greater than 35%, such as greater than 40%.

In an exemplary embodiment, the feedgas in the preheater is heated to a temperature of greater than 1000° F. In an exemplary embodiment, the feedgas in the preheater is heated to a temperature of less than 1500° F., such as less than 1300° F., such as less than 1200° F.

In an exemplary embodiment, the feedgas prior to passing through the reactor further comprises less than 2 mol % water, such as less than 1 mol % water, such as less than 0.5 mol % water, such as less than 0.2 mol % water. In an exemplary embodiment, the offgas comprises between 0 and 2 mol % water, such as 0.1 to less than 2 mol % water, such as between 0 and 1 mol % water.

In an exemplary embodiment, the reaction product stream is cooled to a temperature sufficient to heat the feedgas in the preheater to a temperature of at least 900° F., such as at least 950° F., such as at least 1000° F., but less than 1200° F.

In an exemplary embodiment, the reaction product stream is cooled to a temperature of less than 250° F., such as less than 200° F., such as less than 150° F. in the second quench unit.

Another aspect of the present invention is a self-sustaining process for preparing nitrogen oxide ($NO_x$) (x=1 or 2) from nitrous oxide ($N_2O$), comprising:
continuously passing a preheated feedgas comprising at least 15 mol % $N_2O$ at a rate greater than 1000 pph through a reactor operating at a temperature sufficient to convert the $N_2O$ to $NO_x$ in a yield greater than 20%, wherein heat generated by reaction of the $N_2O$ in the reactor is sufficient to preheat the feedgas prior to entry of the feedgas into the reactor to a temperature that sustains the conversion of the $N_2O$ to $NO_x$.

In an exemplary embodiment of the self-sustaining process, the feedgas comprises at least 20 mol % $N_2O$, such as at least 30 mol % $N_2O$, such as at least 40 mol % $N_2O$, such as at least 50 mol % $N_2O$, such as at least 60 mol % $N_2O$.

In an exemplary embodiment, the feedgas passes through the reactor at a rate of greater than 1000 pph, such as greater than 1500 pph, such as greater than 2000 pph, such as greater than 2500 pph.

In an exemplary embodiment of the self-sustaining process, the sufficient heat generated by reaction of the $N_2O$ is greater than 950° F., such as greater than 1000° F., such as greater than 1200° F., such as greater than 1300° F. In an exemplary embodiment, the sufficient heat is less than 1500° F.

Another aspect of the present invention is a self-sustaining process for preparing nitrogen oxide ($NO_x$) (x=1 or 2) from nitrous oxide ($N_2O$), comprising:
preheating a reactor to a temperature of greater than 1600° F.;
passing a feedgas comprising $N_2O$ through the reactor operating at a temperature sufficient to convert the $N_2O$ to $NO_x$ in a yield greater than 15%,
wherein heat generated by reaction of the $N_2O$ in the reactor is used to preheat the feedgas to a temperature between 900 and 1600° F. prior to entry of the feedgas into the reactor at a rate that does not require application of an external heat source to sustain the conversion.

In an exemplary embodiment of the self-sustaining process, the reactor is preheated to a temperature of greater than 1800° F., such as greater than 1900° F.

In an exemplary embodiment of the self-sustaining process, the reactor operates at a temperature greater than 2000° F., such as greater than 2200° F., such as greater than 2400° F., such as greater than 2600° F., such as greater than 2800° F., such as greater than 3000° F., such as greater than 3200° F. In an exemplary embodiment the reactor operates at a temperature range of 2200 to 3200° F., such as 2200 to 3000° F., such as 2200 to 2800° F., such as 2400 to 3200° F., such as 2400 to 3000° F.

In an exemplary embodiment of the self-sustaining process, an external heat source is used to preheat the interior of the reactor and is optionally used as needed to maintain the reaction occurring in the reactor as self-sustaining.

In an exemplary embodiment of the self-sustaining process, the time between when the feedgas is preheated to when the feedgas enters the reactor is less than 5 seconds, such as less than 3 seconds. In an exemplary embodiment, the time is between 0.01 to 3 seconds, such as 0.25 to 3 seconds.

In an exemplary embodiment of the self-sustaining process, the feedgas prior to passing through the reactor comprises 20 to 80 mol % $N_2O$, such as such as 30 to 70 mol %, such as 30 to 50%, such as 40 to 60%, such as 35 to 70 mol %, such as 40 to 80 mol %, such as 45 to 80 mol %, such as 50 to 80 mol %, such as 60 to 80 mol %.

In an exemplary embodiment of the self-sustaining process, the feedgas prior to passing through the reactor comprises less than 2 mol % water, such as less than 1 mol % water, such as less than 0.5 mol % water, such as less than 0.2 mol % water. In an exemplary embodiment, the feedgas comprises between 0 and 2 mol % water, such as 0.1 to less than 2 mol % water, such as between 0 and 1 mol % water.

Another aspect of the invention is a process for recycling nitric acid, comprising:
reacting nitric acid in a chemical process where at least a portion of the nitric acid is converted to nitrous oxide ($N_2O$);
passing the $N_2O$ through a reactor operating at a temperature of 2200° F. or greater and having a length to diameter ratio (L/D) of greater than 6 to provide nitrogen oxide ($NO_x$) (x=1 or 2) in a yield of greater than 20%;

converting the generated $NO_x$ to nitric acid; and recycling the generated nitric acid for use as a reactant in the same or a different chemical process.

In an exemplary embodiment of the process for recycling nitric acid, the chemical process is the preparation of adipic acid from cyclohexanol and/or cyclohexanone.

In an exemplary embodiment of the process for recycling nitric acid, the $N_2O$ prior to passing through the reactor is present in a gas stream in a concentration of at least 30 mol %, such as at least 40 mol %, such as at least 50 mol %, such as at least 60 mol %, such as at least 70 mol %, such as at least 80 mol %. In an exemplary embodiment, the $N_2O$ concentration is present in a range of 30 to 80 mol %, such as such as 30 to 70 mol %, such as 30 to 50 mol %, such as 40 to 60 mol %, such as 35 to 70 mol %, such as 40 to 80 mol %, such as 45 to 80 mol %, such as 50 to 80 mol %, such as 60 to 80 mol %.

In an exemplary embodiment of the process for recycling nitric acid, the gas stream further comprises less than 2 mol % water, such as less than 1 mol % water, such as less than 0.5 mol % water, such as less than 0.2 mol % water. In an exemplary embodiment, the gas stream comprises between 0 and 2 mol % water, such as 0.1 to less than 2 mol % water, such as between 0 and 1 mol % water.

In an exemplary embodiment of the process for recycling nitric acid, the gas stream is preheated prior to passing through the reactor.

In an exemplary embodiment of the process for recycling nitric acid, the reactor has a length to diameter ratio (L/D) of greater than 4, such as greater than 6, such as greater than 8, such as greater than 10, such as greater than 12, such as greater than 14, such as greater than 16, such as greater than 16. In an exemplary embodiment, the L/D ratio is in a range of 4 to 14, such as 6 to 12, such as 8 to 14, such as 8 to 12, such as 8 to 10, such as 10 to 14, such as 10 to 12.

In an exemplary embodiment of the process for recycling nitric acid, the $N_2O$ has a residence time in the reactor of less than 90 seconds, such as less than 60 seconds, such as less than 30 seconds, such as less than 15 seconds, such as less than 10 seconds, such as less than 5 seconds, such as less than 2 seconds, such as less than 1 second, such as less than 0.5 seconds, such as less than 0.1 seconds. In an exemplary embodiment, the $N_2O$ has a residence time in the reactor of between 0.01 to less than 30 seconds, such as between 0.01 to less than 15 seconds, such as between 0.1 to less than 10 seconds, such as between 0.1 to less than 5 seconds.

In an exemplary embodiment of the process for recycling nitric acid, the recycled nitric acid is used in the same chemical process that originally employed the nitric acid.

In an exemplary embodiment of the process for recycling nitric acid, the recycled nitric acid is used in a different chemical process from the chemical process that originally employed the nitric acid.

Another aspect of the present invention is a nitric acid recovery system, comprising:

a means for generating an offgas comprising nitrous oxide ($N_2O$) in an amount of greater than 20 mol %, where nitric acid is the source of the $N_2O$;

an optional scrubbing unit configured to reduce the amount of other components present in the offgas;

a preheater configured to heat the offgas prior to entry into a reactor;

a reactor configured to thermally convert the $N_2O$ in the offgas to nitrogen oxide ($NO_x$) (x=1 or 2) in a yield of greater than 20% when the gas stream passes through the reactor at a rate greater than 1000 pph; and a means for converting the generated $NO_x$ to nitric acid.

In an exemplary embodiment of the nitric acid recovery system, the means for generating the offgas is a chemical process in which the nitric acid is a reactant and is converted at least in part during the process to the $N_2O$. In a particular embodiment, the chemical process is the preparation of adipic acid.

In an exemplary embodiment of the nitric acid recovery system, the $N_2O$ is present in the offgas in an amount of greater than 20 mol %, such as greater than 40 mol %, such as greater than 60 mol %, such as greater than 80 mol %, such as less than 90 mol %. In an exemplary embodiment, the $N_2O$ is present in an amount of 30 to 90 mol %, such as such as 30 to 70 mol %, such as 30 to 50 mol %, such as 40 to 60 mol %, such as 35 to 70 mol %, such as 40 to 80 mol %, such as 45 to 80 mol %, such as 50 to 80 mol %, such as 60 to 80 mol %.

In an exemplary embodiment of the nitric acid recovery system, the other components present in the offgas that are reduced by the scrubbing unit include one or more of water and $NO_x$.

In an exemplary embodiment of the nitric acid recovery system, the preheater heats the offgas to a temperature of greater than 900° F., such as greater than 950° F., such as greater than 1000° F., such as greater than 1200° F., such as greater than 1400° F., but less than 1500° F.

In an exemplary embodiment of the nitric acid recovery system, the reactor operates at a temperature greater than 2000° F., such as greater than 2200° F., such as greater than 2400° F., such as greater than 2600° F., such as greater than 2800° F., such as greater than 3000° F. In an exemplary embodiment the reactor operates at a temperature range of 2200 to 3000° F., such as 2200 to 2800° F., such as 2300 to 2800° F., such as 2400 to 2800° F.

In an exemplary embodiment of the nitric acid recovery system, the reactor has a length to diameter ratio (L/D) of greater than 4, such as greater than 6, such as greater than 8, such as greater than 10, such as greater than 12, such as greater than 14, such as greater than 16, such as greater than 18. In an exemplary embodiment, the L/D ratio is in a range of 6 to 14, such as 6 to 12, such as 8 to 14, such as 8 to 12, such as 8 to 10, such as 10 to 14, such as 10 to 12.

In an exemplary embodiment of the nitric acid recovery system, the gas stream passes through the reactor at a rate greater than 1500 pph, such as greater than 2000 pph, such as greater than 2500 pph, such as greater than 3000 pph, such as greater than 5000 pph, such as greater than 10,000 pph, such as greater than 20,000 pph, such as greater than 30,000 pph, such as greater than 40,000 pph, such as greater than 50,000 pph, such as greater than 60,000 pph, such as greater than 70,000 pph, such as greater than 80,000 pph, such as greater than 90,000 pph. In another exemplary embodiment, the gas stream passes through the reactor at a rate of 3000 to 100,000 pph, such as 3000 to 80,000 pph, such as 3000 to 50,000 pph, such as 3000 to 30,000 pph, such as 3000 to 20,000 pph.

In an exemplary embodiment of the nitric acid recovery system, the means for converting the generated $NO_x$ to nitric acid includes any conventional means.

Another aspect of the present invention is a reaction system configured to convert nitrous oxide ($N_2O$) to nitric acid, comprising:

a preheater configured to heat an incoming gas stream comprising at least 10 mol % $N_2O$ to a temperature of greater than 950° F.;

a plug flow reactor with a length to diameter ratio (L/D) of 4 to 14 connected directly or indirectly to the preheater and configured to thermally convert the $N_2O$ in the gas stream to nitrogen oxide ($NO_x$) (x=1 or 2) in a yield of greater than 20%; and a quench unit connected directly or indirectly to the reactor configured to convert the NOx to nitric acid, where the configuration of the reaction system is substantially "U"-shaped.

In an exemplary embodiment of the reaction system configured to convert nitrous oxide to an intermediate nitric acid stream, the preheater is configured to heat the incoming gas to a temperature of greater than 950° F., such as greater than 1000° F., such as greater than 1200° F., such as greater than 1400° F., but less than 1500° F.

In an exemplary embodiment of the reaction system configured to convert nitrous oxide to an intermediate nitric acid stream, the incoming gas stream comprises at least 30 mol % $N_2O$, such as at least 40 mol %, such as at least 50 mol %, such as at least 60 mol %, such as at least 70 mol %, such as at least 80 mol %. In an exemplary embodiment, the $N_2O$ is present in an amount of 30 to 90 mol %, such as such as 30 to 75 mol %, such as 30 to 50 mol %, such as 40 to 60 mol %, such as 35 to 70 mol %, such as 40 to 80 mol %, such as 45 to 80 mol %, such as 50 to 80 mol %, such as 60 to 80 mol %.

In an exemplary embodiment of the reaction system configured to convert nitrous oxide to an intermediate nitric acid stream, the plug flow reactor has a L/D of 6 to 14, such as 8 to 10, such as 10 to 14, such as 10 to 12.

In an exemplary embodiment of the reaction system configured to convert nitrous oxide to an intermediate nitric acid stream, the quench unit is configured to convert the NOx to nitric acid by any conventional means.

In an exemplary embodiment of the reaction system configured to convert nitrous oxide to an intermediate nitric acid stream, the plug flow reactor is positioned horizontally.

In an exemplary embodiment of the reaction system configured to convert nitrous oxide to an intermediate nitric acid stream, the plug flow reactor has an entry portion with walls sloped at an angle sufficient for maintaining plug flow conditions. In a particular embodiment, the plug flow reactor has an entry portion with walls sloped at an angle of less than 10 degrees, such as less than 8 degrees, such as less than 5 degrees, but greater than 2 degrees.

Another aspect of the present invention is a reaction system for converting nitrous oxide ($N_2O$) to an intermediate nitric acid stream, comprising:

a reactor having a length to diameter (L/D) ratio of greater than 4, where the reactor is configured to thermally convert $N_2O$ present in a gas stream in a concentration of at least 10 mol % to nitrogen oxide ($NO_x$) (x=1 or 2) in a yield of greater than 20%, the reactor containing insulation for maintaining a temperature of between 2200 to 2900° F. on an inner surface of the reactor and a temperature of between 250 to 400° F. on an exterior surface of the reactor; and a means for converting the generated NOx to nitric acid.

In an exemplary embodiment of the reaction system for converting nitrous oxide to nitric acid, the gas stream comprises at least 30 mol % $N_2O$, such as at least 40 mol %, such as at least 50 mol %, such as at least 60 mol %, such as at least 70 mol %, such as at least 80 mol %. In an exemplary embodiment, the $N_2O$ is present in an amount of 30 to 80 mol %, such as such as 30 to 70 mol %, such as 30 to 50 mol %, such as 40 to 60 mol %, such as 35 to 70 mol %, such as 40 to 80 mol %, such as 45 to 80 mol %, such as 50 to 80 mol %, such as 60 to 80 mol %.

In an exemplary embodiment of the reaction system for converting nitrous oxide to an intermediate nitric acid stream, the reactor has a L/D ratio of greater than 6, such as greater than 10, such as greater than 12, such as greater than 14, such as greater than 16, such as greater than 18. In an exemplary embodiment, the L/D ratio is in a range of 8 to 14, such as 8 to 12, such as 8 to 10, such as 10 to 14, such as 10 to 12.

In an exemplary embodiment of the reaction system for converting nitrous oxide to an intermediate nitric acid stream, the temperature of the reactor is maintained at a temperature of between 2200 to 3200° F., such as 2400 to 3000° F., such as 2400 to 2800° F. on an inner surface of the reactor and a temperature of between 300 to 400° F. on an exterior surface of the reactor.

In an exemplary embodiment of the reaction system for converting nitrous oxide to an intermediate nitric acid stream, the means for converting the generated $NO_x$ to nitric acid includes any conventional means.

In an exemplary embodiment of the reaction system for converting nitrous oxide to an intermediate nitric acid stream, the reactor is positioned horizontally or substantially horizontally.

In an exemplary embodiment of the reaction system for converting nitrous oxide to an intermediate nitric acid stream, the reactor has an entry portion with walls sloped at an angle of less than 10 degrees.

Another aspect of the present invention is a reaction system for converting nitrous oxide ($N_2O$) to nitrogen oxide ($NO_x$) (x=1 or 2), comprising:

a preheater configured to heat a feedgas entering a reactor and to cool a reaction product exiting from the reactor;

the reactor configured to convert $N_2O$ to $NO_x$;

a first quench unit configured to cool the reaction product entering the preheater; and an optional second quench unit configured to cool the reaction product downstream of the preheater.

In an exemplary embodiment of the reaction system for converting nitrous oxide to nitrogen oxide, the preheater is configured to heat the feedgas to a temperature of at least 900° F., such as at least 950° F., such as at least 1000° F.

In an exemplary embodiment of the reaction system for converting nitrous oxide to nitrogen oxide, the reaction product entering the preheater is cooled to a temperature of less than 300° F., such as less than 200° F.

In an exemplary embodiment of the reaction system for converting nitrous oxide to nitrogen oxide, the reactor is a plug flow reactor configured to operate at a temperature of 2200 to 3000° F., such as 2400 to 3000° F. on an inner surface of the reactor and a temperature of 200 to 400° F. on an exterior surface of the reactor.

In an exemplary embodiment of the reaction system for converting nitrous oxide to nitrogen oxide, the first quench unit configured to cool the reaction product to a temperature of 1000 to 2000° F., such as 1200 to 1700° F., such as 1200 to 1500° F.

In an exemplary embodiment of the reaction system for converting nitrous oxide to nitrogen oxide, the second quench unit configured to cool the reaction product to a temperature of 100 to 400° F., such as 150 to 300° F., such as 150 to 200° F.

In an exemplary embodiment of the reaction system for converting nitrous oxide to nitrogen oxide, the reaction system is configured to enable substantially adiabatic reaction conditions by utilizing heat of reaction generated during the conversion of $N_2O$ to $NO_x$.

In an exemplary embodiment of the reaction system for converting nitrous oxide to nitrogen oxide, the residence time of the feedgas from the preheater to the reactor is less than 30 seconds, such as less than 20 seconds, such as less than 10 seconds, such as less than 5 seconds, such as less than 3 seconds, such as between 0.01 and 3 seconds.

In an exemplary embodiment of the reaction system for converting nitrous oxide to nitrogen oxide, the preheater and the reactor are configured in a "U"-shape or a substantially "U"-shape.

Another aspect of the present invention is an offgas composition comprising:
at least 15 mol % nitrous oxide ($N_2O$);
less than 2 mol % water; and
less than 1 mol % nitrogen oxide ($NO_x$) (x=1 or 2), wherein the offgas is at a temperature of greater than 900° F.

In an exemplary embodiment, the offgas comprises at least 20 mol % of $N_2O$, such as 30 mol %, such as at least 40 mol %, such as at least 50 mol %, such as at least 60 mol %, such as at least 70 mol %. In an exemplary embodiment, the $N_2O$ is present in an amount of 20 to 90 mol %, such as such as 30 to 80 mol %, 30 to 70 mol %, such as 35 to 80 mol %, such as 35 to 70 mol %, such as 40 to 80 mol %, such as 45 to 80 mol %, such as 50 to 80 mol %, such as 60 to 80 mol %.

In an exemplary embodiment, the offgas comprises less than 1 mol % water.

In an exemplary embodiment, the offgas is at a temperature of greater than 950° F., such as greater than 1000° F., such as greater than 1200° F., such as greater than 1400° F., but less than 1500° F.

In a particular embodiment, the offgas is an offgas resulting from the preparation of adipic acid.

Another aspect of the present invention is the use of recycled nitric acid as a reactant in a chemical process, wherein the nitric acid is recycled by conversion of nitrous oxide ($N_2O$) as a nitric acid degradation product to nitrogen oxide ($NO_x$) (x=1 or 2) in a yield of greater than 15% in a reactor at a temperature of 2200° F. or greater, followed by conversion of the $NO_x$ to nitric acid.

In an exemplary embodiment of the use of recycled nitric acid, the reactor operates at a temperature greater than 2200° F., such as greater than 2400° F., such as greater than 2600° F., such as greater than 2800° F., such as greater than 3000° F. In an exemplary embodiment the reactor operates at a temperature range of 2300 to 3000° F., such as 2400 to 2800° F.

Another aspect of the invention is a process for converting nitrous oxide ($N_2O$) to nitrogen oxide ($NO_x$), comprising:
obtaining a feedgas containing $N_2O$;
optionally subjecting the feedgas to conditions sufficient to increase the concentration of the $N_2O$ in the feedgas;
optionally treating the feedgas to reduce the amount of one or more components present in the feedgas having a negative impact on conversion of the $N_2O$ to $NO_x$;
converting the $N_2O$ in the feedgas to $NO_x$ under any of the reaction conditions described herein (such as by passing the feedgas through a reactor operating at a temperature range sufficient to convert the $N_2O$ to $NO_x$ in a yield of greater than 15%); and
optionally converting the $NO_x$ to a different compound or material.

In an exemplary embodiment, the source of the feedgas is not limited and can be any gas or stream, typically generated in an industrial setting such as a manufacturing facility, that contains nitrous oxide.

In an exemplary embodiment, the means by which the concentration of the nitrous oxide in the feedgas is optionally increased prior to conversion of the nitrous oxide to $NO_x$ is not particularly limited. In a particular embodiment, the concentration of the nitrous oxide in the feedgas is increased to greater than 15 mol %, such as greater than 20 mol %, such as greater than 25 mol %, such as greater than 30 mol %, such as greater than 40 mol %, such as greater than 50 mol %.

In an exemplary embodiment, the feedgas is treated by any conventional means, including those described herein, for reducing the amount of one or more components present in the feedgas having a negative impact on conversion of the $N_2O$ to $NO_x$ prior to treatment of the feedgas under reaction conditions sufficient to convert the nitrous oxide to $NO_x$. In an exemplary embodiment, these components include one or more of water, NO and $NO_2$.

In an exemplary embodiment, the $N_2O$ in the feedgas is converted to $NO_x$ under any of the reaction conditions described herein such as those listed as preferred embodiments (Combinations 1 to 47), which optionally includes preheating of the feedgas prior passage of the feedgas through a reactor operating at a temperature range sufficient to convert the $N_2O$ to nitrogen oxide ($NO_x$) in a yield of greater than 15%. In addition, the reacted gas may optionally be passed through a first quench unit upon exiting the reactor.

In an exemplary embodiment, the $NO_x$ product is converted to a different compound or material, such as a commercially useful compound or material. In a particular embodiment, the $NO_x$ product is converted to nitric acid by any conventional means.

DETAILED DESCRIPTION OF THE INVENTION

Definitions

As used herein, the term "feedstream gas" or "feedstock gas" or "feedstock" or "feedgas" refers to a $N_2O$-containing gas that reacts under the conditions described herein to generate NOx, which is then optionally converted to nitric acid.

As used herein, the term "offgas" refers to a gas that is produced as a by-product or side effect of a process, such as an industrial-scale process. An offgas can be a feedgas.

As used herein, the phrase "conversion reaction" refers to the chemical reaction that occurs in the reactor or reactor zone during which $N_2O$ is converted to $NO_x$ (where x=1 or 2) in a yield of at least 15%. Under the conditions of the conversion reaction, a portion of the $N_2O$ also decomposes to $N_2$ and $O_2$.

As used herein, the phrase "reactant composition" refers to compositions containing $N_2O$ that have not been passed through the reactor—i.e., compositions that have not undergone the conversion reaction. The reactant composition may exist in any physical form but is most commonly present as a gas stream and may also be referred to as a feedstream gas or feedstock gas or feedstock or feedgas or offgas.

As used herein, the phrase "product composition" refers to compositions that have undergone the conversion reaction with the result that the $N_2O$ component of the reactant composition has been oxidized to $NO_x$ in a yield of at least 15%. The product composition may exist in any physical form but is most commonly present as a gas stream.

As used herein, the term "reactor" refers to the place (e.g., the vessel, tube, chamber, pipe or the like) where nitrous oxide ($N_2O$) present in a reactant composition is subjected to thermal reaction conditions under which the $N_2O$ is converted to $NO_x$ (wherein x=1 or 2) in a yield of at least 15%.

As used herein, the terms "nitrous oxide" and "$N_2O$" are used interchangeably.

As used herein, the terms "nitrogen oxide" and "nitrogen oxides" and "$NO_x$" are used interchangeably to describe a mixture of nitrogen monoxide (NO) and nitrogen dioxide ($NO_2$) where x=1 or 2.

As used herein, the phrase "heat of reaction" refers to the heat released as a result of a chemical reaction that is exothermic in nature.

As used herein, the phrase "residence time" or "RT" refers to the period of time that the feedstream gas is present in a particular component (e.g., the preheater, the reactor or the quench unit) of the $N_2O$ conversion system described herein.

As used herein, the phrase "mol %" refers to the percentage that the moles of a particular component represent compared to the total moles that are present.

As used herein, the term "psig" is a commonly used measurement of pressure relative to ambient atmospheric pressure and is quantified in pounds per square inch gauge.

As used herein, the phrase an "adiabatic process" is a process that occurs without transfer of heat or matter between a thermodynamic system and its surroundings.

Reactant Composition Containing $N_2O$

The reactant composition of the present invention is typically in the form of a gas stream, but is not so limited, and is any composition that contains $N_2O$ in an amount of at least 10 mol % up to 100 mol %. Other components may optionally be present in the reactant composition in varying amounts such as, for example, nitrogen monoxide (NO), nitrogen dioxide ($NO_2$), nitrogen ($N_2$), oxygen ($O_2$), water ($H_2O$), carbon dioxide ($CO_2$), inorganic compounds (including metal-containing compounds) and organic molecules (of various molecular weights). Some of these components, such as water and $NO_x$, were observed to have a negative impact on the conversion of $N_2O$ to $NO_x$. In a particular embodiment, the yield of $NO_x$ was observed to decrease by between approximately 0.10% and 1.0%, such as between 0.10% and 0.50% with each 1% increase of water vapor present in the feedstock gas. In another particular embodiment, the yield of $NO_x$ was observed to decrease by between approximately 0.5% and 3.5%, such as 1.0% and 2.0% with each 1% increase of $NO_x$ present in the feedstock gas. As a result, efforts may be taken to reduce the amounts of one or more of these detrimental components before passage of the reactant composition through the reactor, such as by passing the reactant composition through a scrubbing unit (e.g., a knock-out pot or inlet filter).

The source of the reactant composition is not particularly limited and may be, for example, any process that generates $N_2O$ as a by-product. In an exemplary embodiment, the reactant composition is in the form of an offgas from the chemical process for preparing adipic acid. In other embodiments, the source of the reactant composition is the offgas from the production of nitrogen-containing fertilizers such as ammonium nitrate. Nitric acid is a primary ingredient in nitrogen-containing fertilizers and is manufactured by oxidizing ammonia with a platinum catalyst which generates nitrous oxide.

In an exemplary embodiment, the reactant composition comprises greater than 40 mol %, such as greater than 60 mol % $N_2O$, such as greater than 80 mol % $N_2O$. The concentration of $N_2O$ in the reactant composition may be the direct result of a chemical process. Alternatively, the concentration of $N_2O$ in the reactant composition is the result after further concentration by conventional means of the initial concentration of $N_2O$ generated by a chemical process to higher levels. Although it was observed that the yield of $NO_x$ from $N_2O$ decreased with increasing $N_2O$ concentrations in the reactant composition, it was also observed that higher reaction temperatures (for converting $N_2O$ to $NO_x$) were achieved with higher $N_2O$ concentrations. Higher reaction temperatures unexpectedly resulted in higher yields of $NO_x$ which more than offset the loss of yield of $NO_x$ associated with increased $N_2O$ concentration. In a particular embodiment, the yield of NOx was observed to increase with increasing reactor temperature up to approximately 1830° F. where the yield of $NO_x$ remained constant at temperatures up to approximately 2600° F. and reactor residence times ranging from 0.01 seconds to 12 seconds. In addition, higher concentrations of $N_2O$ in the reactant composition desirably resulted in smaller-sized downstream equipment for further processing of the generated NOx, such as its conversion to nitric acid. The cost savings for using smaller-sized equipment is significant when operating on an industrial (commercial) scale. Further, the higher reaction temperatures employed for conversion of the $N_2O$ to $NO_x$ provides a more stable and robust reaction system relative to feed flow and composition. Higher $N_2O$ concentrations and higher reaction temperatures are also preferred for operating the reactor in a self-sustaining manner with no burner assistance required (thus eliminating the negative effects on the yield of $NO_x$ associated with such assistance by, e.g., water-contaminated flue gas) to continuously maintain the conversion reaction.

Pretreatment of the Reactant Composition Prior to Entry into the Reactor

In an exemplary embodiment, the reactant composition (such as in the form of an offgas) is subjected to pretreatment in a preheater unit before its passage through the reactor where the $N_2O$ present in the reactant composition is converted to $NO_x$. The preheater unit performs an important function by heating the reactant composition to a temperature of greater than 800° F., such as greater than 900° F., such as greater than 950° F. to ensure the ability of the conversion reaction occurring in the reactor to continuously sustain itself without the need for an external heat source. In an exemplary embodiment, the heat generated in the reactor by reaction of the $N_2O$ present in the reactant composition is recycled directly or indirectly (such as through one or more cooling quench units) to the preheater unit for the purpose of preheating the reactant composition prior to its passage through the reactor. In an exemplary embodiment, a significant portion of the heat required by the preheater unit for preheating the reactant composition is provided by this heat of reaction generated in the reactor. In another embodiment, substantially all of the heat required by the preheater unit for preheating the reactant composition is provided by the heat of reaction generated in the reactor such that no additional heat source is required.

The degree to which the reactant composition is preheated and the rate at which it is delivered to the reactor is carefully monitored and controlled by the preheater unit in order to maintain an environment in the reactor where the conversion reaction is self-sustaining while avoiding conditions where the conversion reaction becomes too robust and potentially develops into a runaway reaction. If, for example, the temperature in the preheater becomes too high, a controlled amount of water can be introduced into the preheater to lower the temperature. Therefore, the preheater unit represents a highly cost-effective on-demand feature of the present invention that allows for precision control of reaction conditions in the reactor in order to safely achieve optimal mass flow, volume flow and heat flow on a commercial scale.

In another embodiment of the present invention, the preheater unit, in addition to controlling the temperature and rate at which the reactant composition enters the reactor, may also control other properties and aspects of the reactant composition such as, for example, the pressure at which the reactant composition enters the reactor.

Reactor and Reactor Conditions

The reactor, while not limited to a particular design or structure, must be capable of providing the reaction conditions sufficient for conversion of the $N_2O$ present in the reactant composition to $NO_x$ as described herein. In practice, substantially all of the $N_2O$ is consumed when subjected to the reactor conditions and $NO_x$ is obtained in a yield of greater than 15%, such as greater than 17%, such as greater than 18%, such as greater than 20%, such as greater than 21%, such as greater than 23%, such as greater than 25%. In addition to the generation of $NO_x$, a portion of the $N_2O$ degrades to $N_2$ and $O_2$. In an exemplary embodiment, the reactor design is such that the reactor is able to fully operate regardless of whether an external heat source capable of providing on-demand flame assistance is employed to maintain the reactant composition at an optimal temperature range. In a preferred embodiment, the reactor accomplishes this without utilizing moving parts (such as damper valves or retractable devices).

In terms of pressure, it was observed in a particular embodiment that increasing pressure in the reactor had a negative effect on the yield of NOx, with the NOx yield decreasing by between 0.1% and 2.0% (such as 0.5% and 2.0%) with each 10 psig increase in pressure.

In an exemplary embodiment, the interior surface of the reactor comprises a refractory, such as a ceramic (see, e.g., ASTM C71), that would be suitable for use at reactor temperatures of 3000° F. and higher. Such a ceramic material can be clay-based or non-clay-based. Suitable clay-based refractories include fireclay, high-alumina and mullite ceramics. Suitable non-clay refractories include basic, high alumina, silica, silicon carbide, and zircon materials.

In an exemplary embodiment, the interior surface of the reactor comprises refractory in a thickness of 10 to 40 inches, which may optionally include multiple layering of ceramic in the form of tiles or bricks or blocks interspersed with high-temperature insulation wool (such as amorphous alkaline earth silicate wool (AES), aluminosilicate wool (ASW) or polycrystalline wool (PCW)).

The presence of the refractory in the reactor is important for storage of the heat of reaction generated by the exothermic degradation of $N_2O$ to $N_2$ and $O_2$. This heat is then utilized in the endothermic conversion of $N_2O$ to $NO_x$ which facilitates the self-sustaining aspects of the reactor. The presence of the refractory is also important for storing the heat of the preheated reaction composition.

In an exemplary embodiment, the reactor is of a substantially vertical or a substantially horizontal tubular design with a length to diameter ratio (L/D) of at least 4, such as at least 6, such as at least 10, such as at least 12, such as at least 14, such as at least 16, such as at least 18, such as at least 20. In a particular embodiment, the reactor is structurally designed to operate as an adiabatic plug flow reactor with no back mixing of the reactant/product composition (as a gas stream) as it passes through the reactor. In another particular embodiment, the reactor is structurally designed to act substantially as a plug flow reactor but also to provide a limited amount of back mixing of the passing gas stream to achieve a dispersion coefficient that translates into superior yields in the conversion reaction.

In an exemplary embodiment, the reactor is insulated to minimize heat loss through the exterior of the reactor surface (i.e., to maintain adiabatic operation of the reactor). In an exemplary embodiment, the exterior surface of the reactor is maintained at a temperature above 200° F., such as above 250° F., to prevent the possible condensation of nitric acid, which results as NOx generated during the conversion reaction permeates through the interior wall of the reactor and reacts with water (in the form of moisture).

Post-Reactor Conditions

In an exemplary embodiment, the product composition exiting the reactor is cooled by passage through a quench unit (heat exchanger) to a temperature that is sufficient to heat the reactant composition in the preheater to a temperature of at least 900° F., such as at least 1200° F., but lower than 1400° F. In a particular embodiment, the temperature of the product composition (in the form of a gas stream) exiting the reactor is in the range of 2200 to 2900° F. and is cooled to less than 1600° F. by passage through the quench unit and the removed heat is transferred to the preheater to heat the offgas generated from the preparation of adipic acid to a temperature in a range of 900 to 1400° F. before the heated offgas enters the reactor.

In another exemplary embodiment, the cooled product composition (in the form of a gas stream) exits the preheater (from the first quench unit) and passes through a second quench unit (heat exchanger) for further cooling before the NOx present in the product composition gas stream is converted to nitric acid. In a particular embodiment, the temperature of the product composition exiting the preheater is less than 900° F., such as less than 700° F. and is cooled to less than 300° F., such as less than 200° F., by passage through the second quench unit.

Suitable types of quench units include, but are not limited to, direct contact spray quench systems, shell and tube heat exchangers, plate heat exchangers, plate shell heat exchangers and plate fin heat exchangers.

In an exemplary embodiment, the preheater, the reactor and the quench unit(s) exist in a geometric arrangement that is substantially "U"-shaped, which conserves space and is conducive for facilitating the preferred mass, heat and volume transfers for converting $N_2O$ to $NO_x$ on a commercial scale.

Production of Nitric Acid

In an exemplary embodiment, the cooled product composition (in the form of a gas stream) after exiting a first or a second quench unit is at a temperature of less 300° F., such as less than 200° F. The cooled product composition is then optionally compressed to 15 to 150 psig, such as 15 to 100 psig, such as 15 to 50 psig before the NOx present in the composition is converted to nitric acid by any known means, such as those described, for example, in U.S. Pat. Nos. 5,985,230; 5,360,603; 5,266,291; 4,925,639; 4,263,267; 4,235,858; 4,183,906; 4,064,22; 4,062,928; and 4,036,934.

Recycling of the Nitric Acid

The nitric acid that is generated from the product composition may be collected for future use or sale or alternatively, may be recycled as a reactant in the same chemical process that originally resulted in the formation of a $N_2O$- containing composition or in a different chemical process that also employs nitric acid as a reactant where $N_2O$ is generated as a by-product of the reaction.

EXAMPLES

The following examples represent specific embodiments of the present invention and are not intended to otherwise limit the scope of the invention as described herein.

Example 1

A 12-inch section of an empty mullite tube with an internal diameter of 1 inch was heated to 2552° F. by external heating. A feed gas containing 60 mol % $N_2O$, 25 mol % $N_2$, 9 mol % $O_2$ and 6 mol % $CO_2$ was passed through the tube at a pressure of 2.5 psig. The L/D ratio of the reaction zone was equal to 12. The STP residence time was set to 5 seconds. The effluent gas flow was cooled to ambient temperature and the concentrations of NO and $NO_2$ (collectively, $NO_x$) were measured using a chemiluminescence NO—$NO_2$—$NO_x$ analyzer. The calculated yield of $NO_x$ was 20%.

Example 2

A 12-inch section of an empty mullite tube with an internal diameter of 1 inch was heated to 2642° F. by external heating. A feed gas containing 60 mol % $N_2O$, 25 mol % $N_2$, 9 mol % $O_2$ and 6 mol % $CO_2$ was passed through the tube at a pressure of 2.5 psig. The L/D ratio of the reaction zone was equal to 12. The STP residence time was set to 5 seconds. The effluent gas flow was cooled to the ambient temperature and the concentrations of NO and $NO_2$ (collectively, $NO_x$) were measured using a chemiluminescence NO—$NO_2$—$NO_x$ analyzer. The calculated yield of $NO_x$ was 20%.

Example 3

In an example reflective of pilot plant scale, an adipic plant off-gas having a composition of 60 mol % $N_2O$, 25 mol % $N_2$, 2 mol % $O_2$, 6 mol % $CO_2$, 1.2 mol % $H_2O$ and 0.5 mol % NO was passed through a preheater that increased the temperature of the gas to 1200° F. The gas was then passed through a furnace reactor at the rate of 1200 pph. The internal diameter of the reactor was 2 feet and the length of the reaction zone was 24 feet. During the process, natural gas (at a flow of 21 pph) and air (at a flow of 415 pph) was introduced to the front of the reactor as a flue gas from a burner. The temperature in the reactor was 2400° F. The effluent gas flow was cooled to the ambient temperature and the concentrations of NO and $NO_2$ (collectively, $NO_x$) were measured using a chemiluminescence NO—$NO_2$—$NO_x$ analyzer. The calculated yield of $NO_x$ was 16%.

The examples listed in the table below represent the amount of $NO_x$ product predicted by computer simulation when $N_2O$-containing compositions are subjected to reaction conditions associated with the process of the present invention as well as reaction conditions reflective of comparative process conditions. The simulated runs were treated as predictive of the relative impact on the amount of $NO_x$ product produced from various $N_2O$-containing reactant compositions when the identified reaction parameters were varied. The entries in the table represent specific embodiments of the present invention as well as comparative embodiments and are not intended to limit the scope of the present invention as described herein or to limit the influence of any particular reaction parameter (either alone or in combination) on the yield of $NO_x$ product. In the "Yield" column of the table, "A" represents $NO_x$ yields of greater than 23%; "B" represents $NO_x$ yields of 19% up to, but not including, 23%; and "C" represents $NO_x$ yields of less than 19%, where the $NO_x$ yields are based on the amount of $N_2O$ present in the reactant feed. In an exemplary embodiment of the present invention, the "A" examples provide $NO_x$ yields of 24 to 35%, such as 25 to 32%, such as 25 to 30% and the "C" examples provide $NO_x$ yields of less than 17%, such as less than 15%, such as less than 13%, such as less than 10%. In an exemplary embodiment, the "C" examples may be considered as comparative examples, especially when providing yields of less than 15% or less than 13%.

| | Reactant Composition | | | Preheater | Reactor | Process Conditions in Reactor Zone | | | $NO_x$ |
|---|---|---|---|---|---|---|---|---|---|
| Example | $N_2O$ (mol %) | $H_2O$ (wt %) | $NO_x$ (wt %) | Temp (F.) | Temp (F.) | Pressure (psig) | RT (sec) | L/D | Yield (%) |
| 1. | 15 | 0.3 | 0.3 | 1000 | 1700 | 2 | 2 | 6 | C |
| 2. | 15 | 0.3 | 0.3 | 1000 | 2500 | 2 | 2 | 6 | B |
| 3. | 15 | 0.3 | 0.3 | 1000 | 3200 | 2 | 2 | 6 | A |
| 4. | 15 | 0.1 | 0.1 | 1000 | 3200 | 2 | 2 | 6 | A |
| 5. | 15 | 0.3 | 0.3 | 500 | 2800 | 2 | 2 | 6 | A |
| 6. | 15 | 0.3 | 0.3 | 2000 | 2800 | 2 | 2 | 6 | A |
| 7. | 15 | 0.3 | 0.3 | 1000 | 2800 | 10 | 2 | 6 | B |
| 8. | 15 | 0.3 | 0.3 | 1000 | 2800 | 2 | 0.05 | 6 | A |
| 9. | 15 | 0.3 | 0.3 | 1000 | 2800 | 2 | 2 | 18 | A |
| 10. | 15 | 0.3 | 0.3 | 1000 | 2800 | 10 | 0.05 | 18 | A |
| 11. | 15 | 0.3 | 0.3 | 1000 | 2800 | 10 | 20 | 18 | A |
| 12. | 15 | 0.3 | 3.0 | 1000 | 2800 | 2 | 2 | 6 | B |
| 13. | 15 | 3.0 | 0.3 | 1000 | 2800 | 2 | 2 | 6 | B |
| 14. | 15 | 3.0 | 3.0 | 1000 | 2800 | 2 | 2 | 6 | C |
| 15. | 15 | 0.3 | 3.0 | 1000 | 2800 | 10 | 2 | 6 | C |
| 16. | 15 | 3.0 | 0.3 | 1000 | 2800 | 2 | 0.05 | 6 | B |
| 17. | 15 | 0.3 | 3.0 | 1000 | 2800 | 2 | 2 | 18 | B |
| 18. | 15 | 0.3 | 3.0 | 1000 | 2800 | 10 | 0.05 | 18 | B |
| 19. | 15 | 0.3 | 3.0 | 1000 | 2800 | 10 | 20 | 18 | B |
| 20. | 30 | 1.0 | 2.0 | 1100 | 2900 | 10 | 0.1 | 4 | C |
| 21. | 40 | 0 | 1.0 | 900 | 2700 | 2 | 2 | 8 | B |
| 22. | 40 | 0.3 | 0.3 | 1000 | 1700 | 2 | 2 | 6 | C |

-continued

| | Reactant Composition | | | Process Conditions in Reactor Zone | | | | | $NO_x$ |
| | | | | Preheater | Reactor | | | | |
| Example | $N_2O$ (mol %) | $H_2O$ (wt %) | $NO_x$ (wt %) | Temp (F.) | Temp (F.) | Pressure (psig) | RT (sec) | L/D | Yield (%) |
|---|---|---|---|---|---|---|---|---|---|
| 23. | 40 | 0.3 | 0.3 | 1000 | 2500 | 2 | 2 | 6 | B |
| 24. | 40 | 0.3 | 0.3 | 1000 | 3200 | 2 | 2 | 6 | A |
| 25. | 40 | 0.1 | 0.1 | 1000 | 3200 | 2 | 2 | 6 | A |
| 26. | 40 | 0.3 | 0.3 | 500 | 2800 | 2 | 2 | 6 | B |
| 27. | 40 | 0.3 | 0.3 | 2000 | 2800 | 2 | 2 | 6 | B |
| 28. | 40 | 0.3 | 0.3 | 1000 | 2800 | 10 | 2 | 6 | B |
| 29. | 40 | 0.3 | 0.3 | 1000 | 2800 | 2 | 0.05 | 6 | B |
| 30. | 40 | 0.3 | 0.3 | 1000 | 2800 | 2 | 2 | 18 | B |
| 31. | 40 | 0.3 | 0.3 | 1000 | 2800 | 10 | 0.05 | 18 | B |
| 32. | 40 | 0.3 | 0.3 | 1000 | 2800 | 10 | 20 | 18 | B |
| 33. | 40 | 0.3 | 3.0 | 1000 | 2800 | 2 | 2 | 6 | C |
| 34. | 40 | 3.0 | 0.3 | 1000 | 2800 | 2 | 2 | 6 | B |
| 35. | 40 | 3.0 | 3.0 | 1000 | 2800 | 2 | 2 | 6 | C |
| 36. | 40 | 0.3 | 3.0 | 1000 | 2800 | 10 | 2 | 6 | C |
| 37. | 40 | 3.0 | 0.3 | 1000 | 2800 | 2 | 0.05 | 6 | B |
| 38. | 40 | 0.3 | 3.0 | 1000 | 2800 | 2 | 2 | 18 | B |
| 39. | 40 | 0.3 | 3.0 | 1000 | 2800 | 10 | 0.05 | 18 | C |
| 40. | 40 | 0.3 | 3.0 | 1000 | 2800 | 10 | 20 | 18 | C |
| 41. | 50 | 0.3 | 0.3 | 1000 | 1900 | 2 | 2 | 6 | C |
| 42. | 50 | 0.3 | 0.3 | 1000 | 2200 | 2 | 2 | 6 | C |
| 43. | 50 | 0.3 | 0.3 | 1000 | 2500 | 2 | 2 | 6 | C |
| 44. | 50 | 0.3 | 0.3 | 1000 | 2800 | 2 | 2 | 6 | B |
| 45. | 50 | 0.3 | 1.0 | 1000 | 2800 | 2 | 2 | 6 | B |
| 46. | 50 | 1.0 | 0.3 | 1000 | 2800 | 2 | 2 | 6 | B |
| 47. | 50 | 1.0 | 1.0 | 1000 | 2800 | 2 | 2 | 6 | C |
| 48. | 50 | 1.0 | 2.0 | 1000 | 2800 | 2 | 2 | 6 | C |
| 49. | 50 | 2.0 | 0.5 | 1200 | 2400 | 4 | 10 | 20 | C |
| 50. | 50 | 2.0 | 1.0 | 1000 | 2800 | 2 | 2 | 6 | C |
| 51. | 50 | 0.3 | 0.3 | 1000 | 3100 | 2 | 2 | 6 | B |
| 52. | 50 | 0.3 | 1.0 | 1000 | 3100 | 2 | 2 | 6 | B |
| 53. | 50 | 1.0 | 0.3 | 1000 | 3100 | 2 | 2 | 6 | B |
| 54. | 50 | 1.0 | 1.0 | 1000 | 3100 | 2 | 2 | 6 | B |
| 55. | 50 | 1.0 | 2.0 | 1000 | 3100 | 2 | 2 | 6 | B |
| 56. | 50 | 2.0 | 1.0 | 1000 | 3100 | 2 | 2 | 6 | B |
| 57. | 50 | 0.3 | 0.3 | 1000 | 3400 | 2 | 2 | 6 | A |
| 58. | 50 | 0.3 | 0.3 | 1000 | 2200 | 5 | 2 | 6 | C |
| 59. | 50 | 0.3 | 0.3 | 1000 | 2500 | 5 | 2 | 6 | C |
| 60. | 50 | 0.3 | 0.3 | 1000 | 2800 | 5 | 2 | 6 | B |
| 61. | 50 | 0.3 | 1.0 | 1000 | 2800 | 5 | 2 | 6 | B |
| 62. | 50 | 1.0 | 0.3 | 1000 | 2800 | 5 | 2 | 6 | B |
| 63. | 50 | 1.0 | 1.0 | 1000 | 2800 | 5 | 2 | 6 | B |
| 64. | 50 | 0.3 | 0.3 | 1000 | 3100 | 5 | 2 | 6 | A |
| 65. | 50 | 0.3 | 1.0 | 1000 | 3100 | 5 | 2 | 6 | B |
| 66. | 50 | 1.0 | 0.3 | 1000 | 3100 | 5 | 2 | 6 | B |
| 67. | 50 | 1.0 | 1.0 | 1000 | 3100 | 5 | 2 | 6 | B |
| 68. | 60 | 0.5 | 1.5 | 1400 | 2200 | 1 | 5 | 12 | C |
| 69. | 80 | 0.3 | 0.3 | 1000 | 1700 | 2 | 2 | 6 | C |
| 70. | 80 | 0.3 | 0.3 | 1000 | 2500 | 2 | 2 | 6 | C |
| 71. | 80 | 0.3 | 0.3 | 1000 | 3200 | 2 | 2 | 6 | B |
| 72. | 80 | 0.1 | 0.1 | 1000 | 3200 | 2 | 2 | 6 | B |
| 73. | 80 | 0.3 | 0.3 | 500 | 2800 | 2 | 2 | 6 | C |
| 74. | 80 | 0.3 | 0.3 | 2000 | 2800 | 2 | 2 | 6 | C |
| 75. | 80 | 0.3 | 0.3 | 1000 | 2800 | 10 | 2 | 6 | C |
| 76. | 80 | 0.3 | 0.3 | 1000 | 2800 | 2 | 0.05 | 6 | B |
| 77. | 80 | 0.3 | 0.3 | 1000 | 2800 | 2 | 2 | 18 | B |
| 78. | 80 | 0.3 | 0.3 | 1000 | 2800 | 10 | 0.05 | 18 | C |
| 79. | 80 | 0.3 | 0.3 | 1000 | 2800 | 10 | 20 | 18 | C |
| 80. | 80 | 0.3 | 3.0 | 1000 | 2800 | 2 | 2 | 6 | C |
| 81. | 80 | 3.0 | 0.3 | 1000 | 2800 | 2 | 2 | 6 | C |
| 82. | 80 | 3.0 | 3.0 | 1000 | 2800 | 2 | 2 | 6 | C |
| 83. | 80 | 0.3 | 3.0 | 1000 | 2800 | 10 | 2 | 6 | C |
| 84. | 80 | 3.0 | 0.3 | 1000 | 2800 | 2 | 0.05 | 6 | C |
| 85. | 80 | 0.3 | 3.0 | 1000 | 2800 | 2 | 2 | 18 | C |
| 86. | 80 | 0.3 | 3.0 | 1000 | 2800 | 10 | 0.05 | 18 | C |
| 87. | 80 | 0.3 | 3.0 | 1000 | 2800 | 10 | 20 | 18 | C |

In the process of the present invention, increasing the amount of water ($H_2O$) and/or the amount of nitrogen oxide ($NO_x$) present in the reactant composition was observed to adversely impact the yield of $NO_x$ product. Increasing the internal temperature of the reactor (particularly to 2500° F. and above, such as to 2800° F. and above) was observed to improve the yield of $NO_x$ product, even in the presence of increasing amounts of yield-decreasing components (such as $H_2O$ and $NO_x$) in the reactant composition. Increasing the reactor pressure was generally observed to have a negative impact on the yield of $NO_x$ product. Increasing L/D was generally observed to have a positive impact on the yield of $NO_x$ product. Changes in the residence time (RT) of the reactant composition in the reactor (i.e., the length of time that the reactant composition is exposed to the process conditions in the reactor) were generally observed not to have a significant impact on $NO_x$ yield. Regression equations can be generated from collected data and/or from predictive computer simulation results to identify the contributed impact of each of the various reaction parameters for which data was collected, thereby allowing for optimization of $NO_x$ product. When the processes are carried out on an industrial scale, even seemingly modest improvements in NOx yields can prove to be cost-effective in terms of increasing the amount of nitric acid product produced (recycled) from the $N_2O$ initially present in an offgas generated from an industrial process and also in terms of reducing or eliminating the cost associated with conventional (destructive) techniques for disposal of the highly regulated $N_2O$ present in the offgas.

The following exemplary combinations of reactant compositions and process conditions, which represent preferred embodiments of the present invention, are not intended to otherwise limit the full scope of the invention as described herein.

Combination 1: Reactant composition containing 10 to 95 mol % $N_2O$/between 0 to 2.0 mol % $H_2O$/between 0 to 2.0 mol % $NO_x$. Process conditions of preheating the reactant composition to less than 2000° F./feed rate of greater than 3000 pph/internal reactor temperature of 2400 to 3500° F./external surface temperature of reactor greater than 100° F./residence time of less than 30 seconds/reactor pressure of less than 10 psig/reactor L/D of less than 40.

Combination 2: Reactant composition containing 10 to 95 mol % $N_2O$/between 0 to 1.0 mol % $H_2O$/between 0 to 2.0 mol % $NO_x$. Process conditions of preheating the reactant composition to less than 1800° F./feed rate of greater than 3000 pph/internal reactor temperature of 2400 to 3500° F./external surface temperature of reactor greater than 100° F./residence time of less than 30 seconds/reactor pressure of less than 10 psig/reactor L/D of less than 40.

Combination 3: Reactant composition containing 20 to 80 mol % $N_2O$/between 0 to 2.0 mol % $H_2O$/between 0 to 1.0 mol % $NO_x$. Process conditions of preheating the reactant composition to less than 1800° F./feed rate of greater than 3000 pph/internal reactor temperature of 2400 to 3200° F./external surface temperature of reactor greater than 100° F./residence time of less than 30 seconds/reactor pressure of less than 10 psig/reactor L/D of less than 40.

Combination 4: Reactant composition containing 20 to 80 mol % $N_2O$/between 0 to 1.5 mol % $H_2O$/between 0 to 1.5 mol % $NO_x$. Process conditions of preheating the reactant composition to less than 1800° F./feed rate of greater than 3000 pph/internal reactor temperature of 2400 to 3200° F./external surface temperature of reactor greater than 150° F./residence time of less than 15 seconds/reactor pressure of less than 10 psig/reactor L/D of less than 40.

Combination 5: Reactant composition containing 40 to 80 mol % $N_2O$/between 0 to 1.0 mol % $H_2O$/between 0 to 1.0 mol % $NO_x$. Process conditions of preheating the reactant composition to less than 1800° F./feed rate of greater than 3000 pph/internal reactor temperature of 2400 to 3200° F./external surface temperature of reactor greater than 150° F./residence time of less than 15 seconds/reactor pressure of less than 10 psig/reactor L/D of less than 40.

Combination 6: Reactant composition containing 40 to 80 mol % $N_2O$/between 0 to 1.5 mol % $H_2O$/between 0 to 1.5 mol % $NO_x$. Process conditions of preheating the reactant composition to less than 1800° F./feed rate of greater than 3000 pph/internal reactor temperature of 2600 to 3200° F./external surface temperature of reactor greater than 150° F./residence time of less than 15 seconds/reactor pressure of less than 10 psig/reactor L/D of less than 40.

Combination 7: Reactant composition containing 40 to 80 mol % $N_2O$/between 0 to 1.0 mol % $H_2O$/between 0 to 1.0 mol % $NO_x$. Process conditions of preheating the reactant composition to less than 1800° F./feed rate of greater than 3000 pph/internal reactor temperature of 2600 to 3200° F./external surface temperature of reactor greater than 150° F./residence time of less than 15 seconds/reactor pressure of less than 10 psig/reactor L/D of less than 40.

Combination 8: Reactant composition containing 60 to 80 mol % $N_2O$/between 0 to 1.5 mol % $H_2O$/between 0 to 1.5 mol % $NO_x$. Process conditions of preheating the reactant composition to less than 1800° F./feed rate of greater than 3000 pph/internal reactor temperature of 2600 to 3200° F./external surface temperature of reactor greater than 150° F./residence time of less than 15 seconds/reactor pressure of less than 10 psig/reactor L/D of less than 40.

Combination 9: Reactant composition containing 60 to 80 mol % $N_2O$/between 0 to 1.0 mol % $H_2O$/between 0 to 1.0 mol % $NO_x$. Process conditions of preheating the reactant composition to less than 1800° F./feed rate of greater than 3000 pph/internal reactor temperature of 2600 to 3200° F./external surface temperature of reactor greater than 150° F./residence time of less than 15 seconds/reactor pressure of less than 10 psig/reactor L/D of less than 40.

Combination 10: Reactant composition containing 40 to 80 mol % $N_2O$/between 0 to 1.5 mol % $H_2O$/between 0 to 1.5 mol % $NO_x$. Process conditions of preheating the reactant composition to less than 1800° F./feed rate of greater than 3000 pph/internal reactor temperature of 2800 to 3200° F./external surface temperature of reactor greater than 150° F./residence time of less than 15 seconds/reactor pressure of less than 10 psig/reactor L/D of less than 40.

Combination 11: Reactant composition containing 40 to 80 mol % $N_2O$/between 0 to 1.0 mol % $H_2O$/between 0 to 1.0 mol % $NO_x$. Process conditions of preheating the reactant composition to less than 1800° F./feed rate of greater than 3000 pph/internal reactor temperature of 2800 to 3200° F./external surface temperature of reactor greater than 150° F./residence time of less than 15 seconds/reactor pressure of less than 10 psig/reactor L/D of less than 40.

Combination 12: Reactant composition containing 40 to 80 mol % $N_2O$/between 0 to 1.5 mol % $H_2O$/between 0 to 1.5 mol % $NO_x$. Process conditions of preheating the reactant composition to less than 1800° F./feed rate of greater than 3000 pph/internal reactor temperature of 2800 to 3200° F./external surface temperature of reactor greater than 150° F./residence time of less than 15 seconds/reactor pressure of less than 10 psig/reactor L/D of less than 40.

Combination 13: Reactant composition containing 40 to 80 mol % $N_2O$/between 0 to 1.0 mol % $H_2O$/between 0 to 1.0 mol % $NO_x$. Process conditions of preheating the reactant composition to less than 1800° F./feed rate of greater than 3000 pph/internal reactor temperature of 2800 to 3200° F./external surface temperature of reactor greater than 150° F./residence time of less than 15 seconds/reactor pressure of less than 10 psig/reactor L/D of less than 40.

Combination 14: Reactant composition containing 60 to 80 mol % $N_2O$/between 0 to 1.5 mol % $H_2O$/between 0 to 1.5 mol % $NO_x$. Process conditions of preheating the reactant composition to less than 1800° F./feed rate of greater than 3000 pph/internal reactor temperature of 2600 to 3200°

F./external surface temperature of reactor greater than 150° F./residence time of less than 15 seconds/reactor pressure of less than 10 psig/reactor L/D of less than 40.

Combination 15: Reactant composition containing 60 to 80 mol % $N_2O$/between 0 to 1.0 mol % $H_2O$/between 0 to 1.0 mol % $NO_x$. Process conditions of preheating the reactant composition to less than 1800° F./feed rate of greater than 3000 pph/internal reactor temperature of 2600 to 3200° F./external surface temperature of reactor greater than 150° F./residence time of less than 15 seconds/reactor pressure of less than 10 psig/reactor L/D of less than 40.

Combination 16: Reactant composition containing 60 to 80 mol % $N_2O$/between 0 to 1.5 mol % $H_2O$/between 0 to 1.5 mol % $NO_x$. Process conditions of preheating the reactant composition to less than 1800° F./feed rate of greater than 3000 pph/internal reactor temperature of 2800 to 3200° F./external surface temperature of reactor greater than 150° F./residence time of less than 15 seconds/reactor pressure of less than 10 psig/reactor L/D of less than 40.

Combination 17: Reactant composition containing 60 to 80 mol % $N_2O$/between 0 to 1.0 mol % $H_2O$/between 0 to 1.0 mol % $NO_x$. Process conditions of preheating the reactant composition to less than 1800° F./feed rate of greater than 3000 pph/internal reactor temperature of 2800 to 3200° F./external surface temperature of reactor greater than 150° F./residence time of less than 15 seconds/reactor pressure of less than 10 psig/reactor L/D of less than 40.

Combination 18: Reactant composition containing 20 to 80 mol % $N_2O$/between 0 to 0.5 mol % $H_2O$/between 0 to 0.5 mol % $NO_x$. Process conditions of preheating the reactant composition to less than 1800° F./feed rate of greater than 3000 pph/internal reactor temperature of 2400 to 3200° F./external surface temperature of reactor greater than 100° F./residence time of less than 30 seconds/reactor pressure of less than 10 psig/reactor L/D of less than 40.

Combination 19: Reactant composition containing 40 to 80 mol % $N_2O$/between 0 to 0.5 mol % $H_2O$/between 0 to 0.5 mol % $NO_x$. Process conditions of preheating the reactant composition to less than 1800° F./feed rate of greater than 3000 pph/internal reactor temperature of 2400 to 3200° F./external surface temperature of reactor greater than 150° F./residence time of less than 15 seconds/reactor pressure of less than 10 psig/reactor L/D of less than 40.

Combination 20: Reactant composition containing 40 to 80 mol % $N_2O$/between 0 to 0.5 mol % $H_2O$/between 0 to 0.5 mol % $NO_x$. Process conditions of preheating the reactant composition to less than 1800° F./feed rate of greater than 3000 pph/internal reactor temperature of 2400 to 3200° F./external surface temperature of reactor greater than 150° F./residence time of less than 15 seconds/reactor pressure of less than 10 psig/reactor L/D of less than 40.

Combination 21: Reactant composition containing 40 to 80 mol % $N_2O$/between 0 to 0.5 mol % $H_2O$/between 0 to 0.5 mol % $NO_x$. Process conditions of preheating the reactant composition to less than 1800° F./feed rate of greater than 3000 pph/internal reactor temperature of 2600 to 3200° F./external surface temperature of reactor greater than 150° F./residence time of less than 15 seconds/reactor pressure of less than 10 psig/reactor L/D of less than 40.

Combination 22: Reactant composition containing 40 to 80 mol % $N_2O$/between 0 to 0.5 mol % $H_2O$/between 0 to 0.5 mol % $NO_x$. Process conditions of preheating the reactant composition to less than 1800° F./feed rate of greater than 3000 pph/internal reactor temperature of 2600 to 3200° F./external surface temperature of reactor greater than 150° F./residence time of less than 15 seconds/reactor pressure of less than 10 psig/reactor L/D of less than 40.

Combination 23: Reactant composition containing 60 to 80 mol % $N_2O$/between 0 to 0.5 mol % $H_2O$/between 0 to 0.5 mol % $NO_x$. Process conditions of preheating the reactant composition to less than 1800° F./feed rate of greater than 3000 pph/internal reactor temperature of 2600 to 3200° F./external surface temperature of reactor greater than 150° F./residence time of less than 15 seconds/reactor pressure of less than 10 psig/reactor L/D of less than 40.

Combination 24: Reactant composition containing 60 to 80 mol % $N_2O$/between 0 to 0.5 mol % $H_2O$/between 0 to 0.5 mol % $NO_x$. Process conditions of preheating the reactant composition to less than 1800° F./feed rate of greater than 3000 pph/internal reactor temperature of 2600 to 3200° F./external surface temperature of reactor greater than 150° F./residence time of less than 15 seconds/reactor pressure of less than 10 psig/reactor L/D of less than 40.

Combination 25: Reactant composition containing 40 to 80 mol % $N_2O$/between 0 to 0.5 mol % $H_2O$/between 0 to 0.5 mol % $NO_x$. Process conditions of preheating the reactant composition to less than 1800° F./feed rate of greater than 3000 pph/internal reactor temperature of 2800 to 3200° F./external surface temperature of reactor greater than 150° F./residence time of less than 15 seconds/reactor pressure of less than 10 psig/reactor L/D of less than 40.

Combination 26: Reactant composition containing 40 to 80 mol % $N_2O$/between 0 to 0.5 mol % $H_2O$/between 0 to 0.5 mol % $NO_x$. Process conditions of preheating the reactant composition to less than 1800° F./feed rate of greater than 3000 pph/internal reactor temperature of 2800 to 3200° F./external surface temperature of reactor greater than 150° F./residence time of less than 15 seconds/reactor pressure of less than 10 psig/reactor L/D of less than 40.

Combination 27: Reactant composition containing 40 to 80 mol % $N_2O$/between 0 to 0.5 mol % $H_2O$/between 0 to 0.5 mol % $NO_x$. Process conditions of preheating the reactant composition to less than 1800° F./feed rate of greater than 3000 pph/internal reactor temperature of 2800 to 3200° F./external surface temperature of reactor greater than 150° F./residence time of less than 15 seconds/reactor pressure of less than 10 psig/reactor L/D of less than 40.

Combination 28: Reactant composition containing 40 to 80 mol % $N_2O$/between 0 to 0.5 mol % $H_2O$/between 0 to 0.5 mol % $NO_x$. Process conditions of preheating the reactant composition to less than 1800° F./feed rate of greater than 3000 pph/internal reactor temperature of 2800 to 3200° F./external surface temperature of reactor greater than 150° F./residence time of less than 15 seconds/reactor pressure of less than 10 psig/reactor L/D of less than 40.

Combination 29: Reactant composition containing 60 to 80 mol % $N_2O$/between 0 to 0.5 mol % $H_2O$/between 0 to 0.5 mol % $NO_x$. Process conditions of preheating the reactant composition to less than 1800° F./feed rate of greater than 3000 pph/internal reactor temperature of 2600 to 3200° F./external surface temperature of reactor greater than 150° F./residence time of less than 15 seconds/reactor pressure of less than 10 psig/reactor L/D of less than 40.

Combination 30: Reactant composition containing 60 to 80 mol % $N_2O$/between 0 to 0.5 mol % $H_2O$/between 0 to 0.5 mol % $NO_x$. Process conditions of preheating the reactant composition to less than 1800° F./feed rate of greater than 3000 pph/internal reactor temperature of 2600 to 3200° F./external surface temperature of reactor greater than 150° F./residence time of less than 15 seconds/reactor pressure of less than 10 psig/reactor L/D of less than 40.

Combination 31: Reactant composition containing 60 to 80 mol % $N_2O$/between 0 to 0.5 mol % $H_2O$/between 0 to 0.5 mol % $NO_x$. Process conditions of preheating the reactant composition to less than 1800° F./feed rate of greater than 3000 pph/internal reactor temperature of 2800 to 3200° F./external surface temperature of reactor greater than 150° F./residence time of less than 15 seconds/reactor pressure of less than 10 psig/reactor L/D of less than 40.

Combination 32: Reactant composition containing 60 to 80 mol % $N_2O$/between 0 to 0.5 mol % $H_2O$/between 0 to 0.5 mol % $NO_x$. Process conditions of preheating the reactant composition to less than 1800° F./feed rate of greater than 3000 pph/internal reactor temperature of 2800 to 3200° F./external surface temperature of reactor greater than 150° F./residence time of less than 15 seconds/reactor pressure of less than 10 psig/reactor L/D of less than 40.

Combination 33: Reactant composition containing 20 to 80 mol % $N_2O$/between 0 to 0.5 mol % $H_2O$/between 0 to 0.5 mol % $NO_x$. Process conditions of preheating the reactant composition to less than 1800° F./feed rate of greater than 10,000 pph/internal reactor temperature of 2400 to 3200° F./external surface temperature of reactor greater than 200° F./residence time of less than 30 seconds/reactor pressure of less than 5 psig/reactor L/D of less than 20.

Combination 34: Reactant composition containing 40 to 80 mol % $N_2O$/between 0 to 0.5 mol % $H_2O$/between 0 to 0.5 mol % $NO_x$. Process conditions of preheating the reactant composition to less than 1800° F./feed rate of greater than 10,000 pph/internal reactor temperature of 2400 to 3200° F./external surface temperature of reactor greater than 200° F./residence time of less than 15 seconds/reactor pressure of less than 5 psig/reactor L/D of less than 20.

Combination 35: Reactant composition containing 40 to 80 mol % $N_2O$/between 0 to 0.5 mol % $H_2O$/between 0 to 0.5 mol % $NO_x$. Process conditions of preheating the reactant composition to less than 1800° F./feed rate of greater than 10,000 pph/internal reactor temperature of 2400 to 3200° F./external surface temperature of reactor greater than 200° F./residence time of less than 15 seconds/reactor pressure of less than 5 psig/reactor L/D of less than 20.

Combination 36: Reactant composition containing 40 to 80 mol % $N_2O$/between 0 to 0.5 mol % $H_2O$/between 0 to 0.5 mol % $NO_x$. Process conditions of preheating the reactant composition to less than 1800° F./feed rate of greater than 10,000 pph/internal reactor temperature of 2600 to 3200° F./external surface temperature of reactor greater than 200° F./residence time of less than 15 seconds/reactor pressure of less than 5 psig/reactor L/D of less than 20.

Combination 37: Reactant composition containing 40 to 80 mol % $N_2O$/between 0 to 0.5 mol % $H_2O$/between 0 to 0.5 mol % $NO_x$. Process conditions of preheating the reactant composition to less than 1800° F./feed rate of greater than 10,000 pph/internal reactor temperature of 2600 to 3200° F./external surface temperature of reactor greater than 200° F./residence time of less than 15 seconds/reactor pressure of less than 5 psig/reactor L/D of less than 20.

Combination 38: Reactant composition containing 60 to 80 mol % $N_2O$/between 0 to 0.5 mol % $H_2O$/between 0 to 0.5 mol % $NO_x$. Process conditions of preheating the reactant composition to less than 1800° F./feed rate of greater than 10,000 pph/internal reactor temperature of 2600 to 3200° F./external surface temperature of reactor greater than 200° F./residence time of less than 15 seconds/reactor pressure of less than 5 psig/reactor L/D of less than 20.

Combination 39: Reactant composition containing 60 to 80 mol % $N_2O$/between 0 to 0.5 mol % $H_2O$/between 0 to 0.5 mol % $NO_x$. Process conditions of preheating the reactant composition to less than 1800° F./feed rate of greater than 10,000 pph/internal reactor temperature of 2600 to 3200° F./external surface temperature of reactor greater than 200° F./residence time of less than 15 seconds/reactor pressure of less than 5 psig/reactor L/D of less than 20.

Combination 40: Reactant composition containing 40 to 80 mol % $N_2O$/between 0 to 0.5 mol % $H_2O$/between 0 to 0.5 mol % $NO_x$. Process conditions of preheating the reactant composition to less than 1800° F./feed rate of greater than 10,000 pph/internal reactor temperature of 2800 to 3200° F./external surface temperature of reactor greater than 200° F./residence time of less than 15 seconds/reactor pressure of less than 5 psig/reactor L/D of less than 20.

Combination 41: Reactant composition containing 40 to 80 mol % $N_2O$/between 0 to 0.5 mol % $H_2O$/between 0 to 0.5 mol % $NO_x$. Process conditions of preheating the reactant composition to less than 1800° F./feed rate of greater than 10,000 pph/internal reactor temperature of 2800 to 3200° F./external surface temperature of reactor greater than 200° F./residence time of less than 15 seconds/reactor pressure of less than 5 psig/reactor L/D of less than 20.

Combination 42: Reactant composition containing 40 to 80 mol % $N_2O$/between 0 to 0.5 mol % $H_2O$/between 0 to 0.5 mol % $NO_x$. Process conditions of preheating the reactant composition to less than 1800° F./feed rate of greater than 10,000 pph/internal reactor temperature of 2800 to 3200° F./external surface temperature of reactor greater than 200° F./residence time of less than 15 seconds/reactor pressure of less than 5 psig/reactor L/D of less than 20.

Combination 43: Reactant composition containing 40 to 80 mol % $N_2O$/between 0 to 0.5 mol % $H_2O$/between 0 to 0.5 mol % $NO_x$. Process conditions of preheating the reactant composition to less than 1800° F./feed rate of greater than 10,000 pph/internal reactor temperature of 2800 to 3200° F./external surface temperature of reactor greater than 200° F./residence time of less than 15 seconds/reactor pressure of less than 5 psig/reactor L/D of less than 20.

Combination 44: Reactant composition containing 60 to 80 mol % $N_2O$/between 0 to 0.5 mol % $H_2O$/between 0 to 0.5 mol % $NO_x$. Process conditions of preheating the reactant composition to less than 1800° F./feed rate of greater than 10,000 pph/internal reactor temperature of 2600 to 3200° F./external surface temperature of reactor greater than 200° F./residence time of less than 15 seconds/reactor pressure of less than 5 psig/reactor L/D of less than 20.

Combination 45: Reactant composition containing 60 to 80 mol % $N_2O$/between 0 to 0.5 mol % $H_2O$/between 0 to 0.5 mol % $NO_x$. Process conditions of preheating the reactant composition to less than 1800° F./feed rate of greater than 10,000 pph/internal reactor temperature of 2600 to 3200° F./external surface temperature of reactor greater than 200° F./residence time of less than 15 seconds/reactor pressure of less than 5 psig/reactor L/D of less than 20.

Combination 46: Reactant composition containing 60 to 80 mol % $N_2O$/between 0 to 0.5 mol % $H_2O$/between 0 to 0.5 mol % $NO_x$. Process conditions of preheating the reactant composition to less than 1800° F./feed rate of greater than 10,000 pph/internal reactor temperature of 2800 to 3200° F./external surface temperature of reactor greater than 200° F./residence time of less than 15 seconds/reactor pressure of less than 5 psig/reactor L/D of less than 20.

Combination 47: Reactant composition containing 60 to 80 mol % $N_2O$/between 0 to 0.5 mol % $H_2O$/between 0 to 0.5 mol % $NO_x$. Process conditions of preheating the reactant composition to less than 1800° F./feed rate of greater than 10,000 pph/internal reactor temperature of 2800 to 3200° F./external surface temperature of reactor greater than 200° F./residence time of less than 15 seconds/reactor pressure of less than 5 psig/reactor L/D of less than 20.

All publications and patents cited herein are incorporated by reference in their entireties.

The invention claimed is:

1. A process for preparing adipic acid, comprising:
reacting at least one of cyclohexanone and cyclohexanol with nitric acid to produce adipic acid and an offgas comprising at least 10 mol % nitrous oxide ($N_2O$);
converting the $N_2O$ present in the offgas to nitrogen oxide ($NO_x$) (x=1 or 2) in a yield of greater than 15% by passing the offgas through a reactor operating at a temperature of 2400° F. or greater and wherein the reactor operates at a pressure of 15 psig of less;
converting the $NO_x$ to nitric acid; and
optionally recycling the nitric acid to produce additional adipic acid.

2. The process according to claim 1, wherein the reactor operates at a temperature range of 2400 to 3500° F.

3. The process according to claim 1, wherein the offgas prior to passing through the reactor comprises 15 to 90 mol % $N_2O$.

4. The process according to claim 1, wherein the offgas prior to passing through the reactor further comprises less than 2 mol % water.

5. The process according to claim 1, wherein the reactor has a length to diameter ratio (L/D) of 3 to 30.

6. The process according to claim 1, wherein the offgas passes through the reactor at a rate of greater than 1000 pph.

7. The process according to claim 1, wherein the offgas prior to passing through the reactor further comprises less than 2 mol % $NO_x$.

8. The process according to claim 1, wherein the offgas prior to passing through the reactor is preheated to greater than 900° F.

9. The process according to claim 1, wherein the offgas prior to passing through the reactor is treated to reduce an amount of at least one of water and $NO_x$ present in the offgas.

10. A self-sustaining process for preparing nitrogen oxide ($NO_x$) (x=1 or 2) from nitrous oxide ($N_2O$), comprising:
preheating a reactor to a temperature of greater than 1600° F.;
passing a feedgas comprising $N_2O$ through the reactor operating at a temperature of 2400 to 3500° F. and wherein the reactor operates at a pressure of 15 psig of less;
wherein heat generated by reaction of the $N_2O$ in the reactor is used to preheat the feedgas to a temperature between 900 and 1600° F. prior to entry of the feedgas into the reactor at a rate that does not require application of an external heat source to sustain the conversion, and
wherein the $N_2O$ is converted to $NO_x$ in a yield of greater than 15%.

11. The self-sustaining process according to claim 10, wherein the feedgas prior to passing through the reactor comprises 30 to 80 mol % $N_2O$.

12. The self-sustaining process according to claim 10, wherein the feedgas prior to passing through the reactor comprises less than 2 mol % water.

13. A process for converting nitrous oxide ($N_2O$) to nitrogen oxide ($NO_x$) x=1 or 2), comprising:
obtaining a feedgas containing $N_2O$;
optionally subjecting the feedgas to conditions sufficient to increase the concentration of the $N_2O$ in the feedgas;
optionally treating the feedgas to reduce the amount of one or more components present in the feedgas having a negative impact on conversion of the $N_2O$ to $NO_x$;
converting the $N_2O$ in the feedgas to NO by passing the feedgas through a reactor operating at a temperature of 2400 to 3500° F. and wherein the reactor operates at a pressure of 15 psig of less; and
optionally converting the $NO_x$ to a different compound or material,
wherein the $N_2O$ is converted to $NO_x$ in a yield of greater than 15%.

14. The process according to claim 13, wherein the feedgas prior to passing through the reactor comprises 40 to 80 mol % $N_2O$.

15. The process according to claim 13, wherein the one or more components present in the feedgas having a negative impact on conversion of the $N_2O$ to $NO_x$ include water, NO and $NO_2$.

* * * * *